United States Patent [19]

Eibl

[11] Patent Number: 5,153,179

[45] Date of Patent: Oct. 6, 1992

[54] MEDICAMENT WITH IMPROVED PENETRATION OF THE TISSUE MEMBRANE

[75] Inventor: Hansjörg Eibl, Bovenden, Fed. Rep. of Germany

[73] Assignee: Max-Planck-Gesellschaft Zur Foerderung Der Wissenschaften e.V., Göttingen, Fed. Rep. of Germany

[21] Appl. No.: 689,115

[22] PCT Filed: Nov. 28, 1984

[86] PCT No.: PCT/EP84/00372

§ 371 Date: Jul. 24, 1985

§ 102(e) Date: Jul. 24, 1985

[87] PCT Pub. No.: WO85/02342

PCT Pub. Date: Jun. 6, 1985

Related U.S. Application Data

[63] Continuation of Ser. No. 762,195, Jul. 24, 1985, abandoned.

[30] Foreign Application Priority Data

Dec. 1, 1983 [DE] Fed. Rep. of Germany ....... 3343530

[51] Int. Cl.⁵ .............................. A61K 31/70
[52] U.S. Cl. ........................ 514/34; 514/90; 514/249; 514/274; 514/283; 514/654; 514/772; 514/946; 568/567; 568/675; 568/680
[58] Field of Search ............. 514/90, 34, 946, 283, 514/32, 654, 274, 249, 772; 568/567, 675, 680

[56] References Cited

U.S. PATENT DOCUMENTS 4,393,073 7/1983 Boguth et al. ................ 514/546 X
4,562,075 12/1985 Rajadhyaksha .................. 514/946

OTHER PUBLICATIONS

Dyer, H. M., An Index of Tumor Chemotherapy, Mar., 1949, pp. 10-12, 149, 154 and 155.

*Primary Examiner*—José G Dees
*Attorney, Agent, or Firm*—Felfe & Lynch

[57] ABSTRACT

A composition useful as a medicament with improved penetration of cell membranes comprising an active material and a compound of general formula:

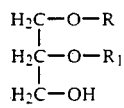

wherein either residue $R_1$ or $R_2$ is an alkyl, alkylene, alkynyl or alkoxy group of 3-7 carbon atoms, and the other residue is a hydrogen atom, together with pharmaceutical additives and dilution agents.

9 Claims, 2 Drawing Sheets

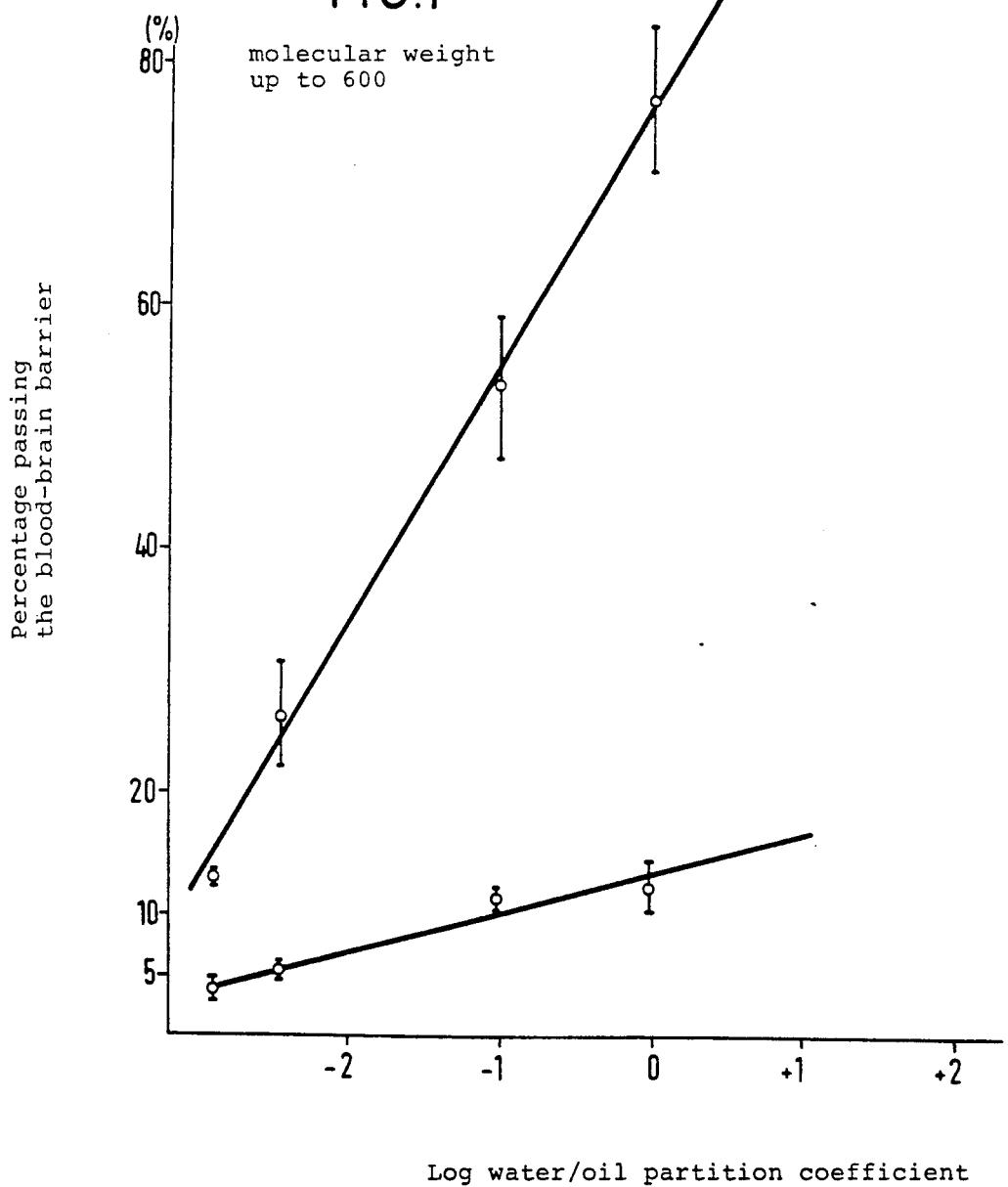

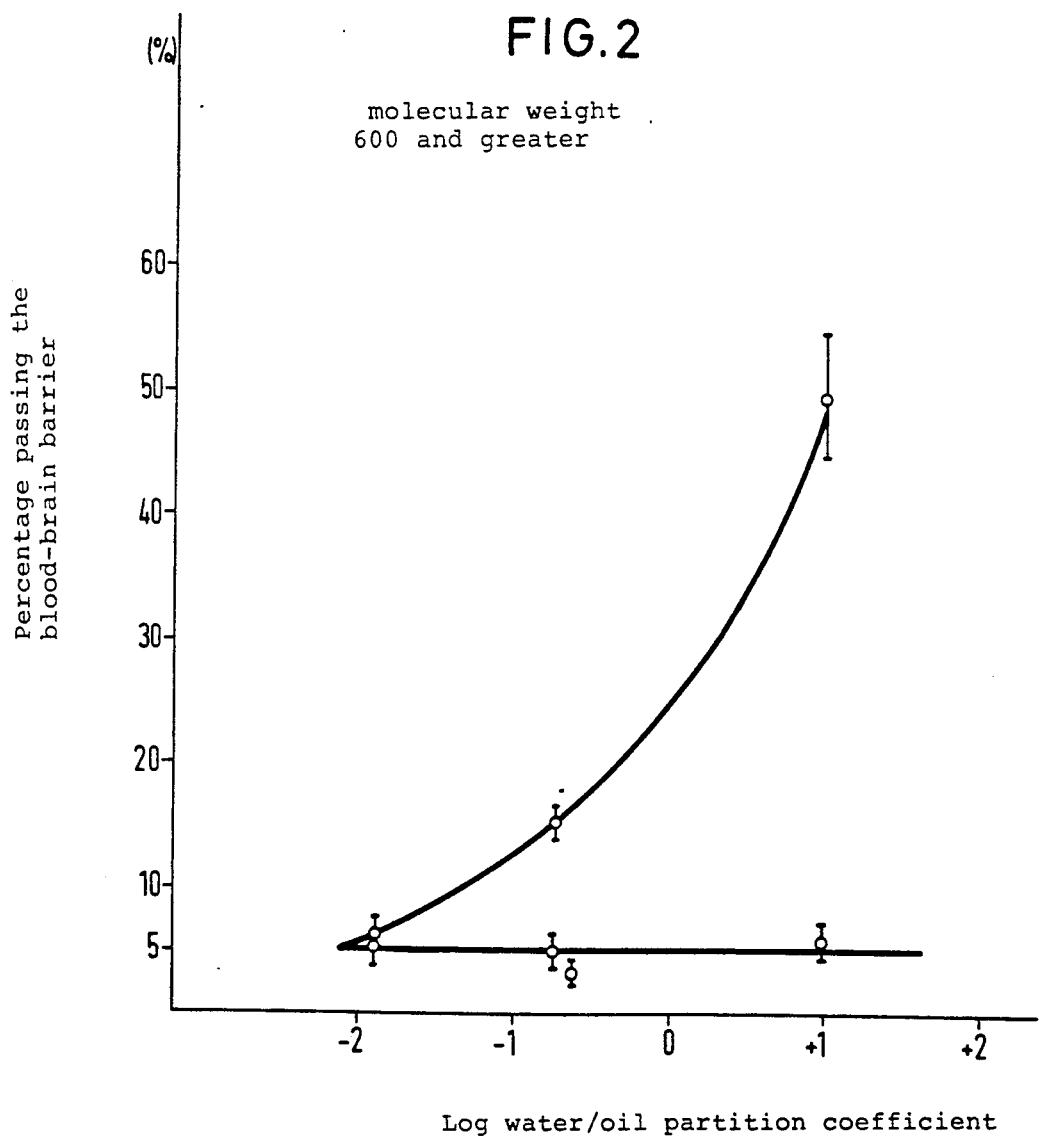

MEDICAMENT WITH IMPROVED PENETRATION OF THE TISSUE MEMBRANE

This application is a continuation of application Ser. No. 06/762,195, filed Jul. 24, 1985, abandoned.

DESCRIPTION

The invention concerns a medicament which makes possible an improved penetration of the active material through the tissue membrane or barrier of the object organ.

A known problem in the case of the administration of medicaments consists in that the actual active material frequently can only poorly pass the cell membrane so that either the per se possible actions of the medicament cannot in practice be achieved or the active material must be overdosed to such an extent that the undesired side actions, especially in organs other than the object organ, are increased.

Especially problematical in this regard is the co-called blood-brain barrier. The normal blood brain barrier is a highly selective permeability barrier which prevents the blood/brain transfer of many compounds. This especially marked barrier has its anatomical basis in the capillary vessels which display special structural characteristics. The ability of an active material in free solution (i.e. not bound to protein) in the blood plasma to penetrate the blood-brain barrier is substantially determined by the ability of the active material itself to separate out of the plasma and to penetrate into the lipid of the endothelial cell plasma membranes. If no specific mechanism is here present, the lipid solubility is the important factor which causes the penetration of the active material through the blood-brain barrier so long as the molecular weight of the active material is not greater than about 500. Higher molecular active materials are then also not able to penetrate the blood-brain barrier even when the lipid solubility is good.

Therefore, it has already been suggested chemically to modify medicaments by adding a radical with high lipid solubility which makes the penetration into the barrier easier. In the case of suitable choice of this group, it would then again be split off by the metabolism, whereby the active material is liberated in its active form.

A disadvantage of this concept consists in that a modification, which under certain circumstances is difficult to carry out, of the actual active material is necessary and, in the case of the known sensitivity of the effectiveness of medicament active materials to changes in the molecule, activity impairments or new undesired side effects are to be feared.

Similar difficulties as in the case of the blood-brain barrier are also present in the case of other organs, for example in the case of the liver, skin etc.

Therefore, the problem forming the basis of the invention is to solve this problem in a simple way and without change of the actual active material.

According to the invention, this succeeds with a medicament which is characterised in that it consists of an active material in combination with a compound of the general formula

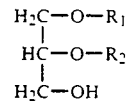

in which one of the residues $R_1$ and $R_2$ signifies an alkyl, alkenyl, alkynyl or alkoxy group with, in each case, 3 to 7 C-atoms and the other residue signifies an H-atom and conventional pharmaceutical additive and dilution agents.

The compound of the general formula is a glycerol derivative which is substituted in position 1 or in position 2 with one of the above-mentioned short-chained groups. The substituents can be straight-chained or branched and possibly also cyclic and contain up to two double or triple bonds. Typical examples of the compounds according to the invention are 1-n-propylglycerol, 1-n-isopropylglycerol, 1-n-butylglycerol, 1-isobutylglycerol, 1-tert. butylglycerol, 1-n-pentylglycerol, 1-n-hexylglycerol, 1-cyclohexylglycerol and 1-n-heptylglycerol, as well as their isomers 1-methylbutylglycerol, 1-allylglycerol, 1-butynglycerol, the corresponding 2-glycerol compounds, as well as proprionic acid, butyric acid, valeric acid, valeric acid, oenanthic acid, acrylic acid, crotonic acid, angelic acid or tiglic acid, hexenoic acid, heptenoic acid, propionic acid and tetrolic acid esters in position 1 or 2 of the glycerol.

The compounds of the general formula in which $R=H$ are new and, as such, form a subject of the invention.

In the case of the medicament according to the invention, it is important that the active material and the compound of the general formula, in the case of which it is a question of a $C_1$- or $C_2$-glycerol derivative, are used jointly and simultaneously, namely, by injection into a blood vessel which conveys the medicament to the object organ directly and by the shortest possible way. If the object organ of the medicament is the brain, then for the administration there is suitable e.g. the A. carotis. In the case of other organs, the same thing applies. For example, the femoral artery is suitable for administration in the upper leg.

Surprisingly, it has been found that the medicament according to the invention has the result, within seconds after the administration, of an extraordinarily strong increase of the active material concentration in the object organ. It is assumed that the additive contained in the medicament according to the invention, the glycerol derivative of the general formula momentarily opens the tissue barrier, for example the blood-brain barrier, and, in this time, makes possible the entry of the actual active material of the medicament to the object organ. The period of this effect is short and, depending upon the concentration of the glycerol derivative, is to be placed at most about one minute. Thereafter, no noticeable further increase of the active material concentration in the object organ takes place. However, within the said short period of time, it is possible, according to the invention, to increase the dosaging of the actual active material on the other side of the membrane barrier by a multiple.

The effectiveness of the medicament according to the invention was tested according to the method of Oldendorf (Brain-Res., 24, 372–376 (1970)). In the case of this method, the tested active compounds are administered in radioactively marked form and then, after a predetermined time, the radioactivity transferred to the object organ is determined. In the case of the medicament according to the invention, the administration took place into the A. carotis. 15 seconds later, the experimental animal was decapitated, the brain removed and the radioactivity bound therein determined. In the following Table 1 are given the results obtained with this process, namely for 11 different compounds, 9 of which are antitumour agents, namely in the case of administration without addition of a compound of the general formula, with addition of glycerol 1-propyl ether and glycerol 1-pentyl ether. The numerical values give the percentage proportion of active material which has passed the blood-brain barrier. As comparative substance, there was employed an isotonic buffer solution. The compound of the general formula was present in iso-osmolar concentration, which corresponds to about 0.3 Osmol/l. in the solution administered.

TABLE 1

| Substance | without | with $C_3$ | with $C_5$ |
|---|---|---|---|
| endoxan | 11.4 ± 0.4 | 18.9 ± 0.3 | 53.5 ± 6.1 |
| daunomycin | 10.8 ± 2.7 | 24.1 ± 3.3 | 76.8 ± 7.0 |
| methotrexate | 4.7 ± 0.6 | 5.7 ± 1.0 | 26.2 ± 5.8 |
| vinblastine | 5.4 ± 1.7 | 4.2 ± 0.6 | 44.3 ± 6.7 |
| bleomycin | 4.9 ± 1.4 | ./. | 5.7 ± 1.8 |
| peplomycin | 4.5 ± 1.9 | ./. | 13.8 ± 1.5 |
| 5-fluorouracil | 3.7 ± 1.0 | ./. | 13.0 ± 0.1 |
| vepeside | 3.8 ± 0.5 | ./. | 15.2 ± 2.1 |
| ET 18-O-$CH_3$* | 4.5 ± 0.8 | 16.4 ± 4.1 | ./. |
| glycerol | 3.9 ± 1.9 | 11.9 ± 2.9 | 27.4 ± 2.7 |
| phosphatidyl-choline* | 2.6 ± 0.8 | ./. | 16.3 ± 3.3 |
| mitoxandrone | 1.8 ± 0.1 | ./. | 25.1 ± 2.0 |

Analogous experiments were carried out with glycerol compounds substituted in position and gave comparable results.
* dissolved in inger albumin In the case of the experiments according to the method of Oldendorf, the active materials were used in amounts of between 10 and 100 μmol. There was thereby obtained no dependency of the penetration percentage of the active material concentration, i.e. that with increasing amount of active material, the percentage passing the blood-brain barrier remained about the same. In the case of methotrexate as active material, the penetration was also investigated in the case of higher concentrations. It was here found that up to above 10 mMole, a linear increase took place of the proportion of active material advancing to the place of action with practically the same percentage proportion of active material passing the barrier.

The penetration achieved also depends upon the amount of glycerol derivative of the general formula used. Referring to the results given in Table 1, e.g. with endoxan and the $C_3$ additive, there was achieved a penetration of scarcely 20%, whereas with an equal amount of the $C_5$ additive the penetration lay above 50%. However, if one increases the amount of the $C_3$ derivative 2.5 fold, then the percentage penetrating also increases to about 50%.

Analgous experiments were also carried out with other organs and gave fully comparable results. Thus, for example, in the case of a rat extremity, the medicament was administered into the femoralis and the extremity amputated after 30 seconds and divided up into several parts. It was thereby shown that the concentration passing the membrane decreased with increasing distance for the point of administration but was still significantly increased even in the most distant parts.

The additive compound according to the general formula contained in the medicament according to the invention proved to be completely non-toxic. The absence of toxicity of the compounds of the general formula is shown, for example, by the fact that these were administered ip in 50% concentration for three weeks to rats without it being possible to ascertain any kind of disadvantageous actions. In our own experiment, the $C_3$ compounds were administered subcutaneously in 17% concentration without any negative manifestations.

As expedient upper limit, in the case of the derivatives with a radical containing 3 carbon atoms, there is to be regarded a concentration which corresponds to a 30% solution. In the case of the $C_5$ derivatives, the expedient upper limit lies in the region of 5 to 8% of the solution to be injected. In the case of these concentrations, the period of opening, referred to the blood-brain barrier, amounts to about one minute.

The opening times can be determined in that one first injects the compound of the general formula and then, at different times up to a minute thereafter administers the active material. If the distance between the two injections is greater than the opening period, then the membrane barrier has again closed and the percentage of active material taken up is correspondingly low.

The administration expediently takes place as "bolus" injection, whereby initially no substantial mixing of the injected substance with the blood takes place.

The additive compounds of the general formula contained in the medicament according to the invention are rapidly broken down by the liver and are, therefore, no longer detectable in the circulation within the shortest time. This is especially surprising in the case of the compounds in which $R_1 = H$ since an enzyme splitting the 2-O-alkyl position has hitherto not been described.

The choice of the alkylglycerol component according to the general formula for the medicament according to the invention depends, to a certain extent, upon the properties of the actual active material. If the actual active material has no surface-active properties, then the best results were then obtained when $R_1$ or $R_2$ in the compound of the general formula has 5 to 7 C-atoms. If, on the other hand, the active material possesses surface-active properties, then one achieves the best results with a compound of the general formula in which $R_1$ or $R_2$ has 3 to 5 C-atoms.

With regard to the choice of the active material, the medicament according to the invention is subjected to no limitations, i.e. all usual active materials with insufficient penetration into the object organ can be improved by the preparation according to the invention. However, it has been ascertained that, in general, a marked effectiveness is only obtained in the case of active materials with a molecular weight in the range of about 100 to about 3000 and the best results are achieved with those active materials the molecular weight of which lies below 2000, especially in the range of 200 to 1500.

An indication of the usefulness of active materials in the scope of the medicament according to the invention is given by its water/oil partition coefficient. In the accompanying drawing is:

FIG. 1 a graphic representation in which the percentage passing the blood-brain barrier is plotted against the logarithm of the water/oil partition coefficients for the active materials 5-fluorouracil (1), methotrexate (2), endoxan (3) and daunomycin, thus active materials with a molecular weight up to 600. One sees that even in the case of alogarithm −3, admittedly a substantial improvement is still achieved but, with increasing lipophilia, the penetration increases somewhat linearly with the logarithm of the water/oil partition coefficients.

FIG. 2 a graphic representation analogous to FIG. 1 for active materials with a molecular weight lying above 600, namely, bleomycin (5), vepeside or peplomycin (6,7) and vinblastin (8). One sees that in the case of bleomycin with strongly hydrophilic character, the penetration improvement is relatively small, whereas it is increased by more than 25 fold in the case of the most lipophilic of these active materials (after subtraction of the blank value of about 3% for sucrose due to the method).

Since the blood-brain barrier represents the greatest hindrance for chemotherapy from the point of view of the membrane penetration, the medicament according to the invention is especially suitable for active materials which are to act in the brain. These are especially cytostatics but, for example, also psychopharmaceuticals, agents against Parkinson's disease (dopamine) and others.

By means of the use of mixtures of compounds of the general formula, for each active material there can thereby be adjusted certain desired conditions which can easily be monitored according to the method of Oldendorf.

Therefore, the medicament according to the invention makes it possible to bring active materials into the object organ in higher concentrations than hitherto or to achieve the same effects with substantially smaller amount of active material.

The following Examples further explain the invention.

EXAMPLE 1

Preparation of the 1-alkylglycerols

Commercially available 1,2-isopropylideneglycerol, 0.2 mole, is dissolved in 300 ml. tert.-butanol and mixed with 0.3 mole K tert.-butylate. One boils under reflux and mixes dropwise over a period of time of 60 minutes with a solution of alkyl bromide, 0.25 mole, in 100 ml. THF. Thereafter, it is further boiled under reflux for 60 minutes. One cools, mixes with 300 ml. diisopropyl ether and 300 ml. water. The upper phase is evaporated on a rotary evaporator, the oily residue is taken up in 500 ml. $CH_3OH$. mixed with 50 ml. 1N HCl and boiled under reflux. After 60 minutes, the splitting off of the protective groups is complete. One neutralises with $Na_2CO_3$, 0.1 mole, while stirring, filters and removes the solvent in waterpump vacuum. The oily residue is distilled. Table 2 shows the physical data. The yields of pure 1-alkylglycerols lie between 80 and 90%, referred to 1,2-isopropylideneglycerol.

TABLE 2

| 1-alkylglycerol | b.p. | $n_D^{20°}$ C. |
|---|---|---|
| propyl | 83–84° C./0.05 mm. | 1.4420 |
| butyl | 124° C./10 mm. | 1.4444 |
| pentyl | 134° C./10 mm. | 1.4500 |
| hexyl | 141° C./10 mm. | 1.4511 |
| heptyl | 147° C./10 mm. | 1.4525 |

EXAMPLE 2

Preparation of 2-alkylgycerols

Starting from 1,3-benzylideneglycerol, prepared according to Johary and Owen (J. Chem. Soc., 1955, 1299–1301), the alkyl radicals are introduced in the 2-position. For this purpose, 1,3-benzylideneglycerol, 0.2 mole, dissolved in 300 ml. tert.-butanol, was mixed with K tert.-butylate, 0.3 mole, and boiled under reflux. After dropping in of alkyl bromide, 0.25 mole, in 100 ml. THF in a period of time of 60 minutes, it is further heated under reflux for 60 minutes. One cools, mixes with 300 ml. diisopropyl ether and shakes out against 300 ml. water. The upper phase is evaporated on a rotary evaporator, dissolved in 500 ml. methanol and heated under reflux for 30 minutes with 50 ml. 1N HCl. One cools, neutralises with $Na_2CO_3$, 0.1 mole, with stirring and filters. After removal of the solvent in a waterpump vacuum, the oily residue is distilled. Table 3 shows the physical data. The yields of pure 2-alkylglycerols lie between 70 and 80%, referred to 1,3-benzylideneglycerol.

TABLE 2

| 2-alkylglycerol | b.p. | $n_D^{20°}$ C. |
|---|---|---|
| propyl | 126° C./10 mm. | 1.5000 |
| butyl | 134° C./10 mm. | 1.4525 |
| pentyl | 143° C./10 mm. | 1.4554 |
| hexyl | 150° C./10 mm. | 1.4571 |
| heptyl | 156° C./10 mm. | 1.4589 |

SUMMARY

A medicament with improved penetration of the object organ consisting of an active material in combination with a compound of the general formula

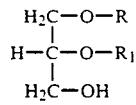

in which one of the residues $R_1$ and $R_2$ signify an alkyl, alkylene, alkynyl or alkoxy group with, in each case, 3 to 7 C-atoms and the other residue signifies an H-atom and conventional pharmaceutical additive and dilution agents.

Two sheets of drawings attached containing FIGS. 1 and 2.

In FIG. 1:
MG bis 600=M.W. up to 600
Log Wasser/Öl-Verteilungskoeffizient=Log water-/oil partition coefficient
In FIG. 2:
MG 600 und größer=M.W. 600 and greater
Log Wasser/Öl-Verteilungskoeffizient=log water-/oil partition coefficient

I claim:

1. Composition comprising an active medicament selected from the group consisting of endoxan, daunomycin, methotrexate, vinblastin, bleomycin, peplomycin, 5-fluorouracil, mitoxandrone, vespeside, ET 18-OCH$_3$, phosphatidylcholine and dopamine and a compound of the formula:

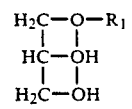

wherein $R_1$ is a straight-chained, branched or cyclic alkyl, alkenyl, or alkynyl group of 3 to 7 carbon atoms, said compound imparting improved cell membrane penetration properties to said composition.

2. Composition of claim 1, wherein said alkyl, alkenyl or alkynyl, has 5 to 7 carbon atoms and said active material is not surface active.

3. Composition of claim 1, wherein said alkyl, alkenyl, or alkynyl group has 3 to 5 carbon atoms and said active medicament is surface active.

4. Composition of claim 1, wherein said active medicament has a molecular weight from about 100 to about 3000.

5. Composition of claim 4, wherein said active medicament has a molecular weight from about 200 to about 1500.

6. Composition of claim 1, wherein the logarithm of the water/oil partition coefficient of the active material is $-3.0$ or greater.

7. Composition of claim 1, wherein said alkyl, alkenyl, or alkynyl, group has 3 to 5 carbon atoms and said compound is present in isoosmolar concentration.

8. Composition of claim 1, wherein said compound is selected from the group consisting of 1-n-propylglycerol, 1-n-isopropylglycerol, 1-n-butylglycerol, 1-isobutylglycerol, 1-tert-butylglycerol, 1-n-pentylglycerol, 1-n-hexylglycerol, 1-cyclohexylglycerol, 1-n-heptylglycerol, 1-methylbutylglycerol, 1-allyglycerol, and 1-butynglycerol.

9. Compositions of claim 1, wherein said compound is selected from the group consisting of glycerol 1-propyl ether or glycerol 1-pentyl ether.

* * * * *